(12) United States Patent
Dextradeur et al.

(10) Patent No.: US 6,805,687 B2
(45) Date of Patent: Oct. 19, 2004

(54) INFUSION PUMP WITH ACCESS REGULATOR

(75) Inventors: Alan J. Dextradeur, Franklin, MA (US); David Konieczynski, Needham, MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 0 days.

(21) Appl. No.: 10/104,784

(22) Filed: Mar. 22, 2002

(65) Prior Publication Data

US 2003/0181888 A1 Sep. 25, 2003

(51) Int. Cl.[7] ................................................. A61M 1/00
(52) U.S. Cl. ..................... 604/151; 604/131; 604/93.01
(58) Field of Search ........................... 604/159, 118, 604/119, 120, 121, 122, 123, 124, 125, 131, 132, 133, 134, 140, 149, 150, 152, 154, 156, 93.01, 153, 288.01, 288.02, 288.03, 288.06, 891.1

(56) References Cited

U.S. PATENT DOCUMENTS

| | | |
|---|---|---|
| 4,557,722 A | 12/1985 | Harris |
| 4,615,691 A * | 10/1986 | Hakim et al. ................ 604/9 |
| 4,772,257 A | 9/1988 | Hakim et al. |
| 4,851,652 A | 7/1989 | Imran |
| 4,978,338 A | 12/1990 | Melsky et al. |
| 5,252,966 A | 10/1993 | Lambropoulos et al. |
| 5,328,465 A | 7/1994 | Kratoska et al. |
| 5,395,324 A | 3/1995 | Hinridhs et al. |
| 5,417,565 A | 5/1995 | Long |
| 5,556,381 A * | 9/1996 | Ensminger et al. ........... 604/93 |
| 5,575,770 A * | 11/1996 | Melsky et al. ................ 604/93 |
| 5,637,083 A * | 6/1997 | Bertrand et al. ............... 604/9 |
| 5,667,504 A | 9/1997 | Baumann et al. |
| 5,769,877 A | 6/1998 | Barreras, Sr. |
| 5,820,589 A | 10/1998 | Torgerson et al. |
| 5,840,063 A | 11/1998 | Flaherty |
| 5,908,414 A | 6/1999 | Otto et al. |
| 6,315,721 B2 | 11/2001 | Schulman et al. |
| 6,319,191 B1 | 11/2001 | Sayet et al. |

OTHER PUBLICATIONS

Cherry, D. A. et al. "A 'Leaking' Synchromed® Pump", Pain 71(1997)109.
Gock, S.B. et al., "Self–Intoxication with morphine obtained from an infusiton pump", J Anal Toxicol 1999 Mar.–Apr.;23(2):130–3.
Partial European Search Report, EP 03 25 1772, Jun. 11, 2003.

* cited by examiner

Primary Examiner—Christopher L. Chin
Assistant Examiner—Ann Y Lam (57) ABSTRACT

An implantable infusion pump for infusing medicine into a patient has a reservoir for holding the medicine, an injection port for injecting medicine into the reservoir and a controllable shield for selectively blocking access to the injection port.

19 Claims, 6 Drawing Sheets

FIG. 11

INFUSION PUMP WITH ACCESS REGULATOR

BACKGROUND

This invention relates to implantable infusion pumps, and more particularly to implantable infusion pumps in which access to drug reservoirs within the pump is controlled.

Implantable infusion pumps are used for the continuous delivery of medicaments, e.g. morphine in a constant dosage over long periods of time. Compared with conventional injections they have the advantage that there is no longer any need to provide an initial high dosage so that despite the decomposition of the medicament up to the next administration time, there is no drop below a certain minimum dose. Instead it is possible to achieve a uniform and significantly reduced supply of the medicament.

The pumps are implanted underneath the skin and are typically designed to be refilled by injecting medication into a reservoir in the pump, the injection penetrating the skin and a septa covering a port into the reservoir. Frequently, the pumps comprise more than one access port. A first access port supplies a reservoir containing medication for long term, slow delivery. A second access port supplies a reservoir which provides a bolus administration of the medication. Typically, all of the medication injected into the second port will be immediately infused into the patient. Incorrect administration of medicine intended for the first port into the second port will provide an overdose of medicine to the patient.

U.S. Pat. No. 5,395,324 solves this problem by providing one or more of the ports with a needle stop and filling the port with needles having a side outlet that is blocked unless inserted into the port to the correct depth by abutting the needle stop. Insertion into the wrong port blocks the outlet and prevents injection.

In addition to the problem of potentially injecting medicine into the wrong port, some patients have highlighted another problem. Especially with medications having an abuse potential, such as morphine, patients have been known to use a syringe to extract the medication from the long term reservoir and then self administer a large dose of the medicine. Such behavior can also lead to an overdose of medicine. The system of the aforementioned '324 patent hinders, but does not completely prevent, such action.

SUMMARY OF THE INVENTION

An implantable infusion pump according to the present invention provides for infusing medication into a patient. The pump comprises a reservoir for containing the medication and an injection access port into the reservoir. An openable and closable shield at the access port blocks access of an injection needle into the port when closed and allows access of the injection needle into the port when open.

The shield can be for instance adapted to move laterally with respect to the access port, or vertically with respect to the access port. Multiple shields can be employed to block access to the port and in addition the shield or shields can employ linear, rotational or other appropriate movement to block an unblock access to the port.

To operate the shield, a magnetic rotor can be provided within the pump coupled to the shield. A magnetic driver external of the pump magnetically couples to the rotor whereby to turn the rotor and operate the shield. The rotor preferably has a sequence of north and south magnetic poles and the driver a complementary sequence of magnetic poles. The sequence of poles can be irregular whereby to make unauthorized access to the pump more difficult. The poles on the driver can be electromagnets.

In one aspect of the invention, a controller can be provided which is in RF communication with a means for opening and closing the shield.

One desirable feature comprises a delay closing mechanism for automatically closing the shield some time period after it is opened so that an operator does not need to remember to close the shield.

A method according to the present invention restricts access to a drug reservoir in an implanted infusion pump which is accessible through an access port. The method comprises the steps of: shielding the access port with a shield during a time when access to the reservoir is not to be allowed; and moving the shield to allow access to the port during a time when access to the reservoir is to be allowed.

DETAILED DESCRIPTION OF THE INVENTION

Figure 1:
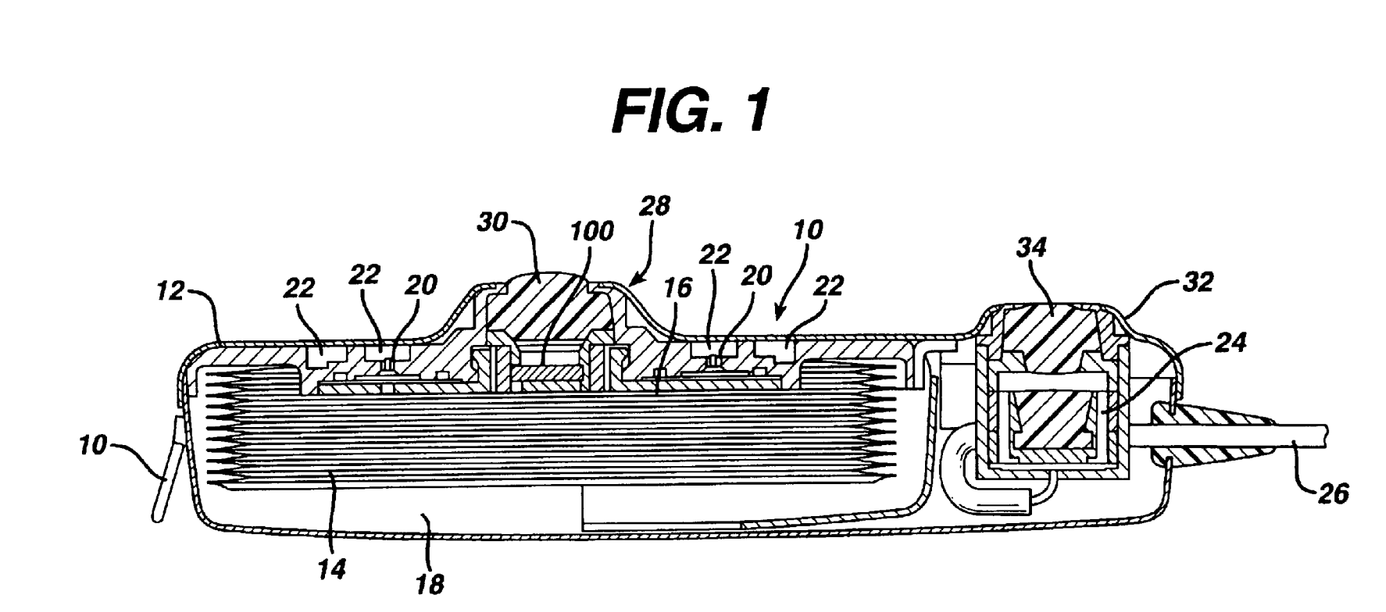
FIG. 1 is a side sectional elevation view of an infusion pump and access regulator according to the present invention.

FIG. 1 illustrates an infusion pump 10 having an outer casing 12 of an inert material, such as for example titanium or stainless steel. A bellows 14 attaches to the shell 12 to form a main reservoir 16 for holding a medicine to be infused into a patient. A gas reservoir 18, formed by the space exterior of the bellows 14 and interior of the casing 12, holds a pressurizing gas to provide a propellant force to urge the medicine out of the main reservoir 16. The main reservoir 16 communicates with valves 20 which in turn lead to a plurality of throttle paths 22, each of which connect to an outlet chamber 24. A catheter connector 26 connects the outlet chamber to a catheter (not shown) which is implanted along with the pump 10 and out of which the medicine flows into the patient.

The valves 6 place one or more of the throttle paths 22 into fluid communication with the main reservoir 16. By varying the flow resistance in the throttle paths 22 the valves 6 can effectively alter the rate at which medicine leaves the pump 10 and enters a patient. A more detailed description of selecting throttle paths, including an RF communication system which induces sufficient current to change the state of the valves is disclosed in U.S. Pat. No. 5,667,504 to Baumann, et al., incorporated herein by reference. In one preferred embodiment, the throttle paths are etched into a chip, such as a silicon wafer chip, as more fully described in U.S. Pat. No. 5,908,414 to Otto, et al., incorporated herein by reference. A more simple pump, may have a single restriction path without an option to change the flow rate.

A raised injection port 28 covered by a septum 30 allows medicine to be injected into the main reservoir 16 with the pump implanted in a patient. A raised bolus injection port 32 covered by a septum 34 allows a bolus of medicine to be injected directly into the outlet chamber 24 where it can quickly flow into the patient.

Implementation of the basic pump as just described is within the knowledge of those skilled in the art and may be varied to suit various needs and future innovations without departing from the scope of the present invention.

An access regulator 100 protects each of the ports 28 and 32 by blocking entry of a needle into the ports 28 and 32. Although several designs are disclosed herein for physically blocking access to the ports 28 and 32, it will be understood by those of skill in the art that other ways of blocking the port can be substituted therefor in the scope and spirit of the present invention.

Figure 2:
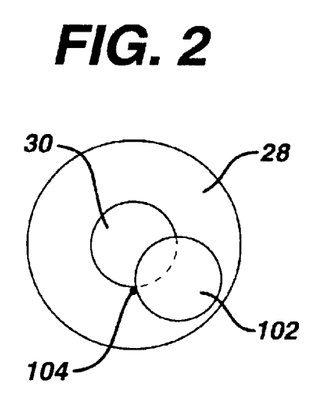
FIG. 2 is a top plan view of a first embodiment of an access regulator for use in the pump of FIG. 1.
Figure 3:
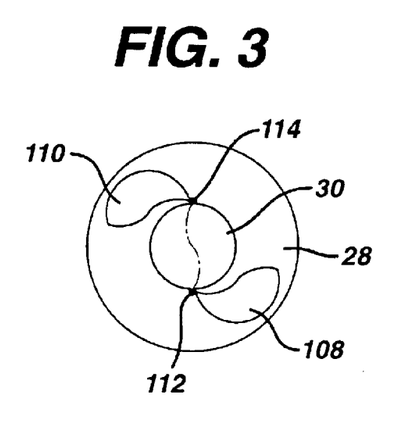
FIG. 3 is a top plan view of a second embodiment of an access regulator for use in the pump of FIG. 1.
Figure 4:
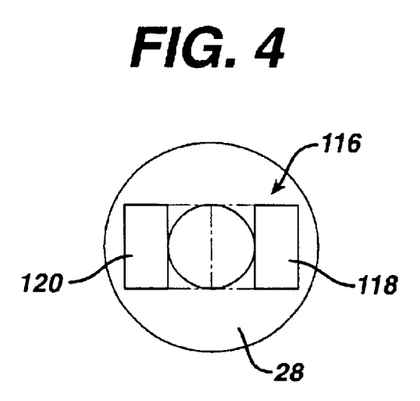
FIG. 4 is a top plan view of a third embodiment of an access regulator for use in the pump of FIG. 1.
Figure 5:
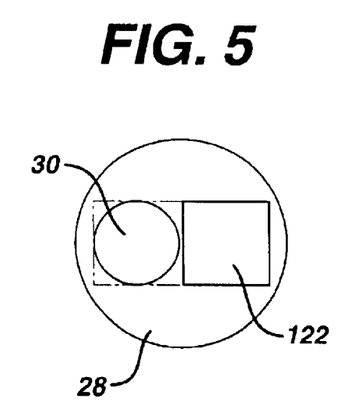
FIG. 5 is a top plan view of a fourth embodiment of an access regulator for use in the pump of FIG. 1.

FIG. 2 illustrates a blocking member comprising a simple cover 102 which pivots laterally about an axis 104 to cover and uncover the port 28. FIG. 3 illustrates a cover 106 in two pieces 108 and 110, each of which rotate laterally about axis 112 and 114 respectively. FIG. 4 illustrates a shutter 116 having two pieces 118 and 120 which slide laterally over the port 28. FIG. 5 illustrates a shutter 122 which slides laterally over the port 28. Other covering methods, such as a mechanical iris, could be substituted therefor.

Figure 6:
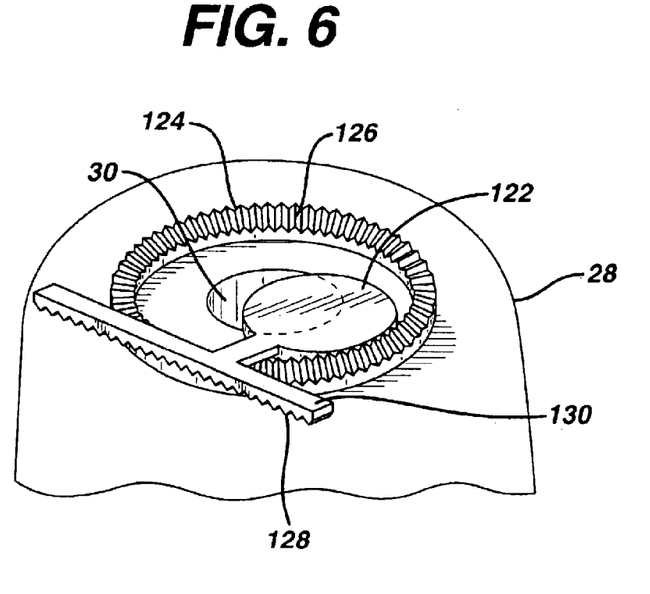
FIG. 6 is a perspective view of a fifth embodiment of an access regulator for use in the pump of FIG. 1.

Preferably, actuation of the access regulator 100 is achieved by rotation of a part within the pump 10. In FIG. 6, a rotor 124 has teeth 126 thereon which engage teeth 128 on a slidable member 130 in a rack and pinion type engagement to translate rotational movement of the rotor 124 into linear movement of the shutter 122 for moving it into a position to block access to or into an alternative position to allow access to the port 28. As further illustrated in FIG. 7, one preferred method of rotating the rotor 124 is via a stepping motor arrangement wherein the rotor 124 carries a series of North magnetic poles 132 and South magnetic poles 134 and an external driver 136 similarly carries a series of North magnetic poles 138 and South magnetic poles 140. Aligning the driver 136 with the rotor 124 and rotating the driver 136 induces rotation in the rotor 124.

Figure 7:
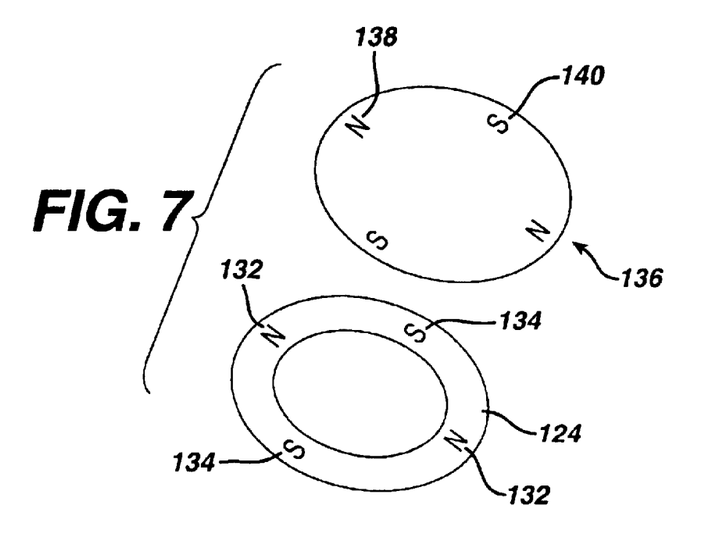
FIG. 7 is a perspective view of a driving mechanism for an access regulator for use in the pump of FIG. 1.
Figure 8:
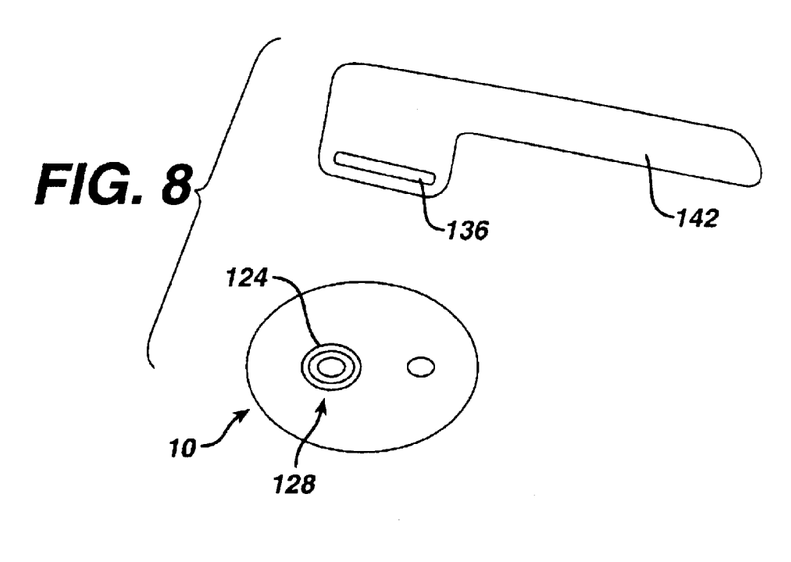
FIG. 8 is a perspective view of the mechanism of FIG. 7 and a controller therefor.

The driver 136 can comprise a simple part manually rotated over the rotor 124, but more preferably comprises a portion of a programmable controller 142 (see FIG. 8). The poles 138 and 140 on the driver 136 can be electromagnets. For more precise operation, stator elements (not shown) complementary to the poles 132 and 134 on the rotor 124 can be positioned in the pump 10 adjacent the rotor 124. Each of the stator elements would be formed of a magnetically soft and permeable material capable of being magnetized by application of a magnetic field, as from the driver 136. Selectively magnetizing the stator elements induces a rotation in the rotor 124. Such a system is more fully described in the Hakim U.S. Pat. Nos. 4,615,691 and 4,772,257, incorporated herein by reference.

The programmable controller 142 can be capable of controlling other aspects of the pump 10 such as the infusion flow rate, or may be dedicated to controlling access to the ports 28 and 32.

Each of ports 28 and 32 preferably has associated therewith a rotor 124 and driver 136 which are incompatible with the rotor and driver of the other port so that the driver for the bolus port 32 will operate only the bolus port and the driver for the regular port will operate only the regular port. Accordingly, opening of the incorrect port is avoided. For instance the arrangement of magnetic poles 134 and 136 on one rotor 124 can be incompatible with the arrangement of magnetic poles 138 and 140 on the other driver 136. Alternatively, the rotors 124 can be given magnetic signatures readable by the controller 142 so that the controller 142 will know which rotor 124 is being controlled.

The methods employed to prevent inadvertent access to the wrong port can also prevent unauthorized access to the port 28 by a patient, for instance the rotor 124 can be keyed with a special sequence of north and south poles. Further security could be provided by a magnetic locking mechanism, not illustrated, in which a magnetic key with a particular magnetic signature must be placed adjacent a magnetic lock within the pump to allow movement of the rotor 124 or of one of the access shields disclosed herein.

Figure 9:
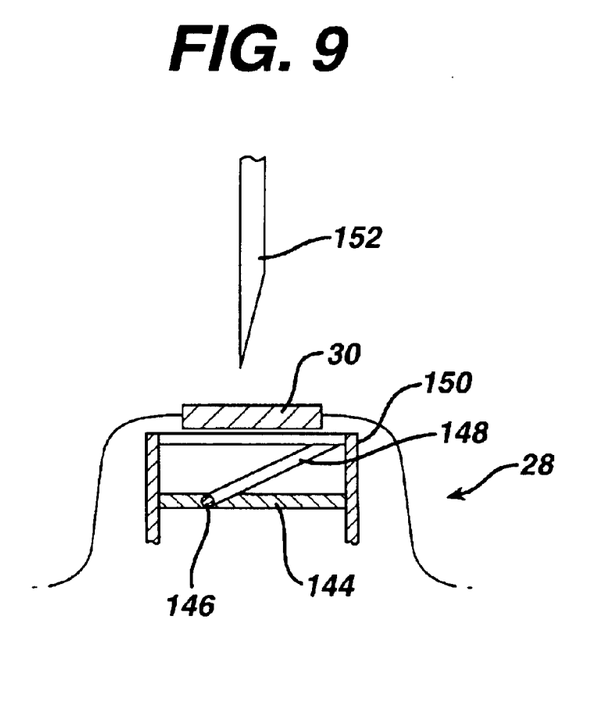
FIG. 9 is a side sectional view of a sixth embodiment of an access regulator for use in the pump of FIG. 1.

FIG. 9 illustrates a further embodiment wherein a needle stop 144 having a cam follower 146 thereon travels axially within the port 28 rather than laterally. The cam follower 146 cams over a spiral camming surface 148 on a rotor 150 to move the needle stop 144 axially. In an upward position it allows passage of a needle 152 through the septa 30 but blocks further entry of the needle 152 into the port 28, thereby preventing medication from entering or exiting the port through the needle 152. In a lowered position the needle 152 is allowed to fully enter the port 28.

To fill the reservoir 16 with the pump 10 implanted in a patient, the operator first opens the access regulator 100 over the injection port 28 and then injects the drug through the patient's skin, through the septum 30 and into the reservoir 16. Afterwards, the operator closes the access regulator 100. For instance with the design of FIGS. 6 and 7, the driver 136 is placed adjacent the rotor 124 and rotated to open the shutter 122 prior to injecting the drug.

Figure 10:
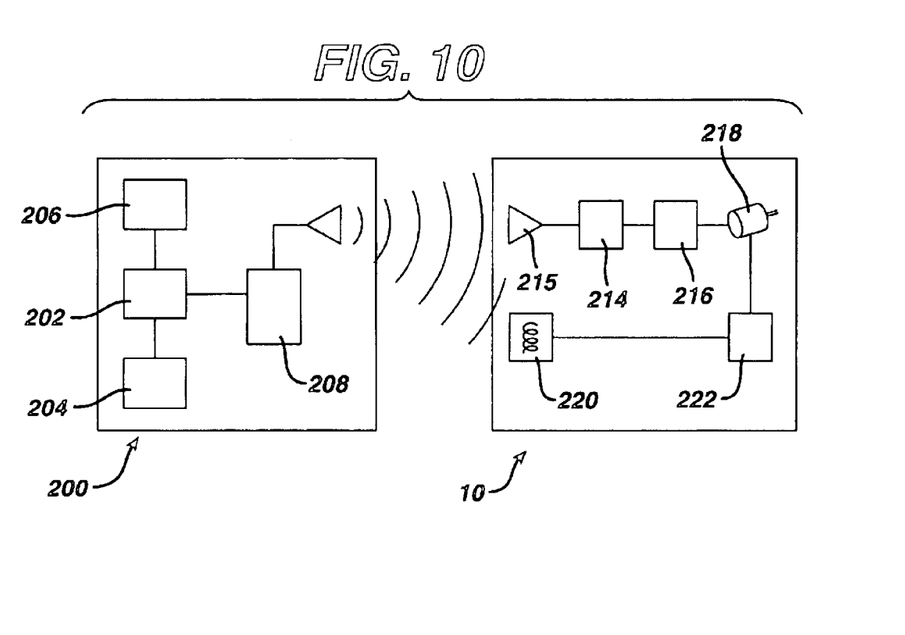
FIG. 10 is a block diagram of a communication system between a controller and a pump according to the invention.

Turning to FIG. 10, radio frequency (RF) communication can be established between the pump 10 and an external controller 200. Such schemes are disclosed in U.S. Pat. Nos. 5,667,504 and 5,820,589 incorporated herein by reference. The controller 200, preferably a hand held device, incorporates control logic, as for instance in the form of a CPU 202 with some means for input such as a keypad 204 and some means for visual output such as a screen 206 or indicator LEDs (not shown), connected to the CPU 202. The CPU further controls an RF transmitter circuit 208 and antenna 210 which transmits instructions through the skin to an antenna 212 in the pump 10. The pump 10 comprises a receiver 214 connected to an antenna 215 and control logic 216 connected to a motor 218 suitable for operating any of the closure mechanisms of the previous embodiments. The motor 218 preferably incorporates or is connected to a power source such as a battery (not shown in FIG. 10).

The power source for the motor could alternatively comprise a coil 220 energized by RF energy transmitted from the controller 200. To increase the instantaneous power to drive the motor 218, the coil 220 could charge a capacitor 222 which is subsequently discharged to operate the motor 218. A limited function controller could be provided so as to provide one or a limited number of openings of the closure mechanism such as for use when a patient is traveling away from his normal physician.

Preferably, the RF communication system of FIG. 10 would not be solely devoted to operating a closure mechanism but could also be used to control other aspects of the pump 10 such as flow rate, etc.

Figure 11:
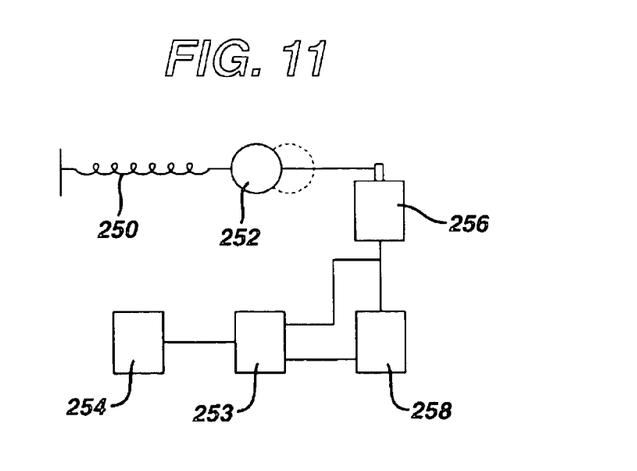
FIG. 11 is a block diagram of an access regulator according to the present invention incorporating an automatic closure upon a time delay.

One desirable feature is a mechanism whereby the closure mechanism is opened, as for instance by any of the methods disclosed in the embodiments herein, and then automatically closed by a delay mechanism. Thus, one would not need to remember to close the mechanism later. FIG. 11 illustrates one such embodiment in which a spring 250 biases a closure door 252 into a closed position. Upon receiving instruction from control logic 253 a battery 254 drives a motor 256 to open the door 252 and also charges a capacitor 258 which, after power from the battery 254 to the motor 256 is removed energizes the motor 256 against the bias of the spring 250 until such time as the charge in the capacitor 258 is dissipated and the spring 250 then closes the door 252. Alternatively, a clock ratchet mechanism (not shown) under power of the spring 250 could time the closure of the door 252.

Although the foregoing description of the preferred embodiments of the present invention has shown, described and pointed out the fundamental novel features of the invention, it will be understood that various omissions, substitutions, and changes in the form of the detail of the apparatus and method as illustrated as well as the uses thereof, may be made by those skilled in the art, without departing from the spirit of the present invention. Consequently, the scope of the present invention should not be limited to the foregoing discussions, but should be defined by the appended claims.

What is claimed is:

1. An implantable infusion pump for infusing medication into a patient, the pump comprising a reservoir for containing the medication and an injection access port into the reservoir, the reservoir being acted upon by a pumping mechanism; and an openable and closable shield at the access port blocking access of an injection needle into the port and into the reservoir when closed and allowing access of the injection needle into the port and into the reservoir when open.

2. An implantable infusion pump according to claim 1 wherein the shield is adapted to move laterally with respect to the access port.

3. An implantable infusion pump according to claim 1 wherein the shield is adapted to move vertically with respect to the access port.

4. An implantable infusion pump according to claim 1 and further comprising:

a magnetic rotor within the pump coupled to the shield; and a magnetic driver external of the pump;

wherein the driver is adapted to couple magnetically with the rotor whereby to turn the rotor and operate the shield.

5. An implantable infusion pump according to claim 4 wherein the rotor has a sequence of north and south magnetic poles and the driver has a complementary sequence of magnetic poles.

6. An implantable infusion pump according to claim 5 wherein the sequence of poles is irregular whereby to make unauthorized access to the pump more difficult.

7. An implantable infusion pump according to claim 5 wherein the poles on the driver are electromagnets.

8. An implantable infusion pump according to claim 1 and further comprising a controller in RE communication with a means for opening and closing the shield.

9. An implantable infusion pump according to claim 5 and further comprising a delay closing means for automatically closing the shield in a time period after opening.

10. A method for restricting access to a drug reservoir in an implanted infusion pump wherein the drug reservoir is accessible through an access port and the reservoir being acted upon by a pumping mechanism, the method comprising the steps of:

shielding the access port and the reservoir with a shield during a time when access to the reservoir is not to be allowed; and moving the shield to allow access to the port and the reservoir during a time when access to the reservoir is to be allowed.

11. A method according to claim 10 wherein the step of moving the shield comprises moving the shield laterally of the port to allow access to the reservoir.

12. A method according to claim 10 wherein the step of moving the shield comprises moving the shield inward of the port to allow a needle to enter the port.

13. A method according to claim 10 and further comprising the steps of:

coupling a magnetic driver, which is external to the pump and positioned outside of a patient's body in proximity to the pump, to a magnetic receiver within the pump;

applying a magnetic force to the magnetic receiver within the pump with the magnetic driver to thereby move the magnetic receiver;

by means of the movement of the magnetic receiver, moving the shield.

14. A method according to claim 13 wherein the magnetic receiver comprises a rotor having at least two opposite poles thereon, and wherein the method further comprises turning the rotor via the magnetic driver and translating rotation of the rotor into movement of the shield.

15. A method according to claim 14 wherein the rotor has a sequence of north and south magnetic poles and the driver has a complementary sequence of magnetic poles.

16. A method according to claim 15 wherein the sequence of poles is irregular whereby to make unauthorized access to the pump more difficult.

17. A method according to claim 15 wherein the poles on the driver are electromagnets and wherein the method comprises selectively energizing the electromagnets so as to move the rotor.

18. A method according to claim 10 further comprising the steps of sending an RE communication from a controller through the skin of a patient to instruct the shield to open.

19. A method according to claim 18 and further comprising the step of automatically closing the shield in a time period after opening the shield.

* * * * *

UNITED STATES PATENT AND TRADEMARK OFFICE
CERTIFICATE OF CORRECTION

PATENT NO. : 6,805,687 B2
DATED : October 19, 2004
INVENTOR(S) : Dextradeur and Konieczynski It is certified that error appears in the above-identified patent and that said Letters Patent is hereby corrected as shown below:

Column 6,
Lines 9 and 56, please delete "RE" and insert -- RF --.
Line 11, please delete "5" and insert -- 8 --.

Signed and Sealed this

Eighteenth Day of January, 2005

JON W. DUDAS
*Director of the United States Patent and Trademark Office*